United States Patent
Moore et al.

(10) Patent No.: US 11,517,356 B2
(45) Date of Patent: Dec. 6, 2022

(54) SPINAL PLATE BENDER

(71) Applicant: K2M, Inc., Leesburg, VA (US)

(72) Inventors: Brandon Moore, Leesburg, VA (US); Clint Boyd, Winchester, VA (US)

(73) Assignee: K2M, Inc., Leesburg, VA (US)

( * ) Notice: Subject to any disclaimer, the term of this patent is extended or adjusted under 35 U.S.C. 154(b) by 168 days.

(21) Appl. No.: 16/576,887

(22) Filed: Sep. 20, 2019

(65) Prior Publication Data

US 2020/0093520 A1    Mar. 26, 2020

Related U.S. Application Data

(60) Provisional application No. 62/733,759, filed on Sep. 20, 2018.

(51) Int. Cl.
*A61B 17/70* (2006.01)
*A61B 17/88* (2006.01)
*A61B 17/00* (2006.01)

(52) U.S. Cl.
CPC ...... *A61B 17/7074* (2013.01); *A61B 17/8863* (2013.01); *A61B 17/7059* (2013.01); *A61B 2017/00367* (2013.01)

(58) Field of Classification Search
CPC ... A61B 17/8863; A61B 17/88; A61B 17/808; A61B 17/8085; A61B 17/80; A61B 17/7074; A61B 17/8858
USPC ................. 606/101.86 B, 101, 866
See application file for complete search history.

(56) References Cited

U.S. PATENT DOCUMENTS

| | | | | |
|---|---|---|---|---|
| 5,651,283 | A * | 7/1997 | Runciman | A61B 17/8863 72/390.4 |
| 6,298,704 | B1 * | 10/2001 | Hoth, III | B21D 7/08 72/173 |
| 6,644,087 | B1 * | 11/2003 | Ralph | A61B 17/8863 72/213 |
| 6,931,908 | B1 * | 8/2005 | Mitson | B21D 7/04 72/213 |
| 2003/0205075 | A1 * | 11/2003 | Strippgen | A61B 17/8863 72/173 |
| 2005/0192577 | A1 * | 9/2005 | Mosca | A61B 17/8863 606/86 B |

(Continued)

OTHER PUBLICATIONS

Extended European Search Report for Application No. EP 19198189.3 dated Feb. 20, 2020, 3 pages.

*Primary Examiner* — Amy R Sipp
(74) *Attorney, Agent, or Firm* — Lerner, David, Littenberg, Krumholz & Mentlik, LLP (57) ABSTRACT

A spinal plate bender includes an actuation assembly, a collet, and a head portion. The actuation assembly includes a housing, a lever pivotably coupled to the housing, a linkage pivotably coupled to the lever, and an actuation shaft operatively coupled with the linkage. The lever is transitionable between a neutral position and an actuated position, which imparts axial displacement to the actuation shaft. The collet includes a proximal section, a sleeve section extending distally from the proximal section, and a coupling section extending distally from the sleeve section. The head portion is configured to support a spinal plate. The head portion includes an anvil portion coupled to a distal end portion of the actuation shaft. The anvil portion is configured to engage a spinal plate to cause bending of a spinal plate supported in the head portion.

20 Claims, 5 Drawing Sheets

(56) References Cited

U.S. PATENT DOCUMENTS

2013/0345759 A1* 12/2013 Meyer ............... A61B 17/7079
606/279
2014/0163617 A1  6/2014 Boachie-Adjei et al.
2015/0012003 A1  1/2015 Ryan et al.

* cited by examiner

SPINAL PLATE BENDER

CROSS REFERENCE TO RELATED APPLICATIONS

The present application claims the benefit of the filing date of U.S. Provisional Patent Application No. 62/733,759 filed Sep. 20, 2018, the disclosure of which is hereby incorporated herein by reference.

BACKGROUND

1. Technical Field

The present disclosure relates to surgical devices and, more particularly, to a spinal plate bender.

2. Discussion of Related Art

The human spinal column is a highly complex structure. It includes twenty-four discrete bones, known as vertebrae, coupled sequentially to one another to house and protect critical elements of the nervous system. In between adjacent vertebrae is a disc. Each disc functions as a shock absorber, absorbing the impact of the body's activities and distributing pressure under compressive loads. Additionally, each disc forms a fibro-cartilaginous joint between adjacent vertebrae, allowing movement of the vertebrae and acting as a ligament to hold the vertebrae together.

For many reasons, such as aging and trauma, the discs may begin to deteriorate and weaken, potentially resulting in chronic pain, degenerative disc disease, or even tearing of the disc. Ultimately, the disc may deteriorate or weaken to the point of herniation, in which the inner portions of the disc protrude through the tear. A herniated disc may press against, or pinch, the spinal nerves, thereby causing radiating pain, numbness, tingling, and/or diminished strength or range of motion. The surgical removal of a damaged or diseased disc is a common procedure in current medical practice. Spinal fusion procedures involve removing a damaged disc and replacing it with an implant such as an intervertebral cage. To keep the implant and the vertebrae fixed in place while bone healing occurs, an external fixation device, such as a spinal plate, is used. Spinal plates are secured to the vertebrae using bone screws, which typically require drilling holes into the vertebrae.

The size of vertebrae and the spacing between vertebrae varies from patient to patient. The height of the vertebrae and the discs between them may vary level by level even in the same person. This typically becomes a problem when working across at least three vertebrae, i.e., when using two level spinal plates. In order to cover the possible range of sizes, health care facilities must carry a large inventory of different sized plates. Another problem is that the holes made into the vertebrae act as a stress concentration within the vertebrae (as would any empty opening or crack within a rigid structural member) and predisposes the vertebrae to bone fracture, screw/plate migration, and/or vertebral failure.

Due to the differences in human spinal columns, particularly deformed spinal columns, during an operation it is desirable to be able to bend a spinal plate to the configuration of the spine to which it is to be connected. Therefore, a continuing need exists for a spinal plate bender that allows a clinician to easily and accurately bend spinal plates prior to insertion into the patient's anatomy.

SUMMARY

In accordance with an embodiment of the present disclosure, a spinal plate bender includes an actuation assembly, a collet, and a head portion. The actuation assembly includes a housing, a lever pivotably coupled to the housing, a linkage pivotably coupled to the lever, and an actuation shaft operatively coupled with the linkage. The lever is transitionable between a neutral position and an actuated position, which imparts axial displacement to the actuation shaft. The collet includes a proximal section, a sleeve section extending distally from the proximal section, and a coupling section extending distally from the sleeve section. The head portion is configured to support a spinal plate. The head portion is coupled to the coupling section of the collet. The head portion includes an anvil portion coupled to a distal end portion of the actuation shaft. The anvil portion is configured to engage a spinal plate to cause bending of a spinal plate supported in the head portion.

In an embodiment, the head portion may include lateral walls defining a gap therebetween. The gap may be dimensioned to receive the anvil portion therein.

In another embodiment, the head portion may define a slot, and the anvil portion may include a pin configured to be slidably received in the slot.

In yet another embodiment, the slot may extend along a longitudinal axis defined by the collet.

In still yet another embodiment, the head portion may include a roller mount and rollers rotatably mounted in the roller mount.

In still yet another embodiment, the rollers and the lateral walls may define a slot dimensioned to support a spinal plate therein.

In another embodiment, each roller may have an hourglass shape.

In yet another embodiment, the anvil portion of the head portion may define an axis extending between the rollers.

In still yet another embodiment, the anvil portion may have a blunt end portion.

In an embodiment, the blunt end portion of the anvil portion may be tapered.

In another embodiment, the head portion may be detachably coupled to the coupling section of the collet.

In an embodiment, the collet may define a lumen having a first portion having a first diameter dimensioned to receive a shoulder of the actuation shaft, and a second portion distal of the first portion and having a second diameter smaller than the first diameter.

In another embodiment, the actuation shaft may include a biasing member disposed about a portion of the actuation shaft distal of the shoulder.

In an embodiment, the second diameter may be dimensioned to receive the portion of the actuation shaft distal of the shoulder and the biasing member.

In yet another embodiment, the lumen of the collet may further include a third portion dimensioned to slidably receive the actuation shaft.

In still yet another embodiment, the collet may include a cutout configured to receive the lever and the linkage extending laterally outward during the transition between the neutral position and the actuated position.

In accordance with another aspect of the present disclosure, a method of bending a spinal plate includes placing at least a portion of a spinal plate in a slot defined in a head portion of a spinal plate bender, the spinal plate bender including an actuation shaft and an anvil portion configured to engage a spinal plate in a proximal position, the slot disposed between a roller mount including rollers, and lateral walls of the head portion and advancing the anvil portion into the head portion such that the anvil portion presses against a portion of a spinal plate in the head portion In an embodiment, placing the spinal plate bender in a neutral position may include placing a lever operatively coupled with the actuation shaft via a linkage, at an acute angle with respect to a longitudinal axis defined by the spinal plate bender.

In another embodiment, advancing the anvil portion may include placing a lever operatively coupled with the actuation shaft via a linkage, in parallel with a longitudinal axis defined by the spinal plate bender.

In yet another embodiment, advancing the anvil portion may include slidably advancing a pin of the anvil portion within a slot defined in the head portion.

In yet another embodiment, advancing the anvil portion may include advancing the anvil portion in a direction orthogonal to the slot of the head portion.

BRIEF DESCRIPTION OF THE DRAWINGS

Various aspects of the present disclosure are described hereinbelow with reference to the drawings, wherein.

DETAILED DESCRIPTION

The presently disclosed spinal plate bender will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As shown in the drawings and as described throughout the following description, and as is traditional when referring to relative positioning on an object, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is farther from the clinician during proper use. In addition, the term "cephalad" is used in this application to indicate a direction toward a patient's head, whereas the term "caudad" indicates a direction toward the patient's feet. Further still, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front.

With reference to FIGS. 1-4, a spinal plate bender in accordance with an embodiment of the present disclosure is generally shown as a plate bender 100. The plate bender 100 is configured to deform a surgical implant such as, e.g., a spinal plate, to a desired shape (e.g., curvature) to meet the needs of a particular surgical procedure. The plate bender 100 includes an actuation assembly 200, a collet 300 configured receive at least a portion of the actuation assembly 200 therein, and a head portion 400 configured to support a spinal plate therein. The spinal plate may generally be substantially planar or contoured in either or both the cephalad/caudad and/or medial/lateral planes. The spinal plate may generally define at least two bone screw portals such as, e.g., holes or slots, that provide a through passage that communicates from a top side of the spinal plate through to an underside of the spinal plate. The at least two bone screw portals are sized and configured to permit the passage of a shank portion of each of a corresponding bone fixation element, which may be bone screws for fixation of the spinal plate to underlying bone. The spinal plate may be employed to fix, e.g., one or multiple, vertebral levels. Reference may be made to U.S. Patent Application Publication No. 2018/0070992, the entire contents of which are incorporated herein by reference, for a detailed discussion of the construction and operation of a spinal plate usable with the presently disclosed plate bender 100.

Figures 1, 2:
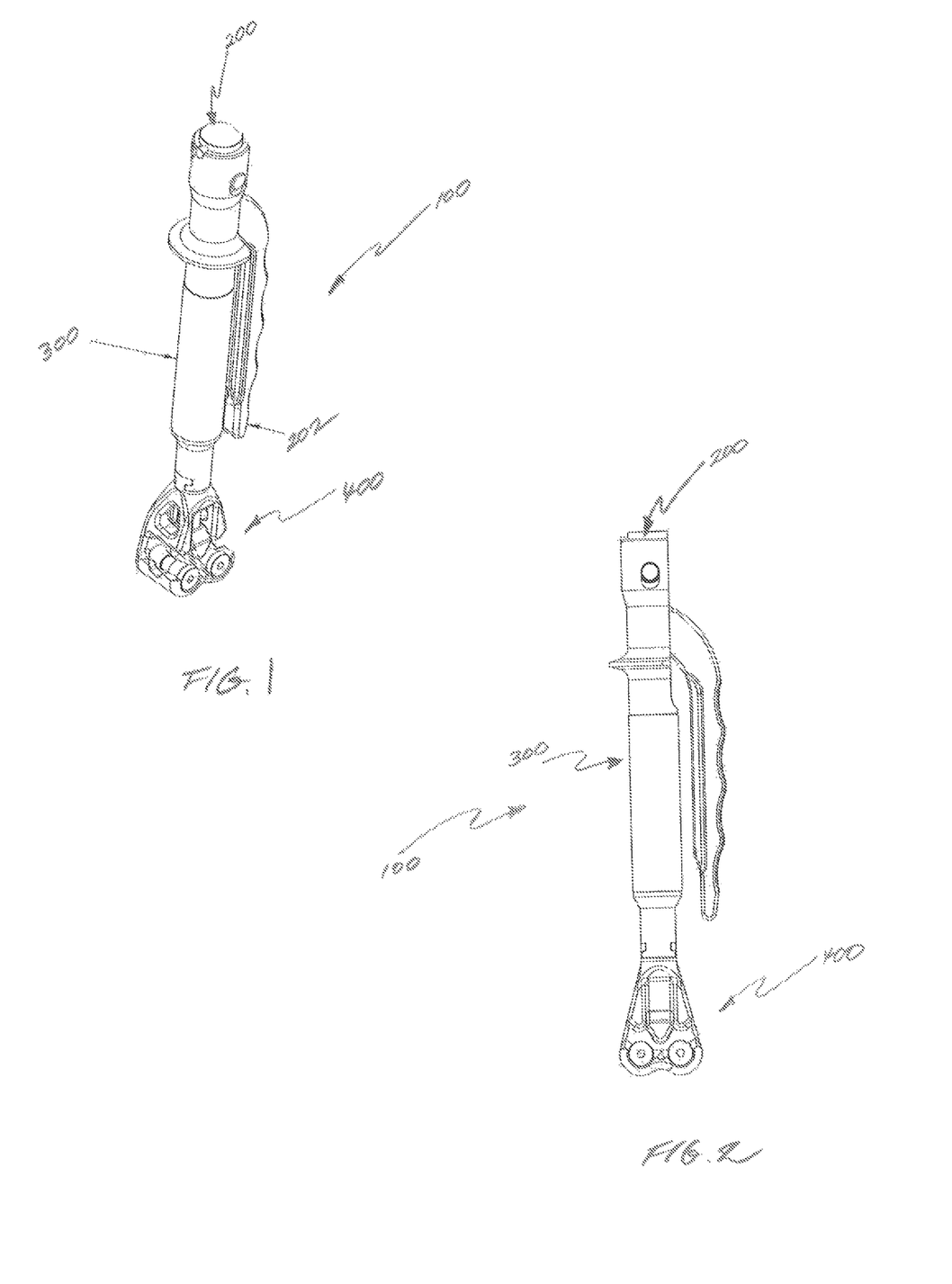
FIG. 1 is a perspective view of a spinal plate bender in accordance with an embodiment of the present disclosure.
FIG. 2 is a front view of the spinal plate bender of FIG. 1.
Figure 3:
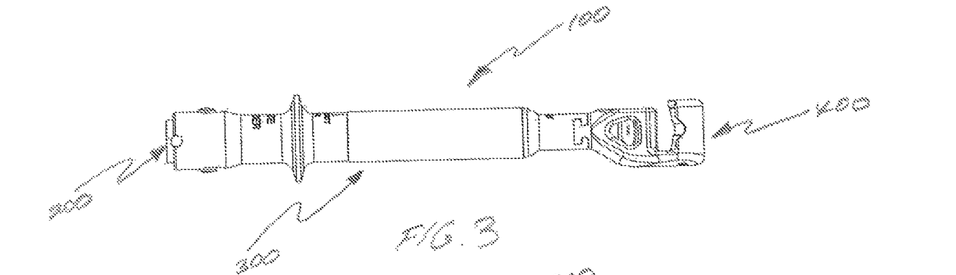
FIG. 3 is a side view of the spinal plate bender of FIG. 1.
Figure 4:
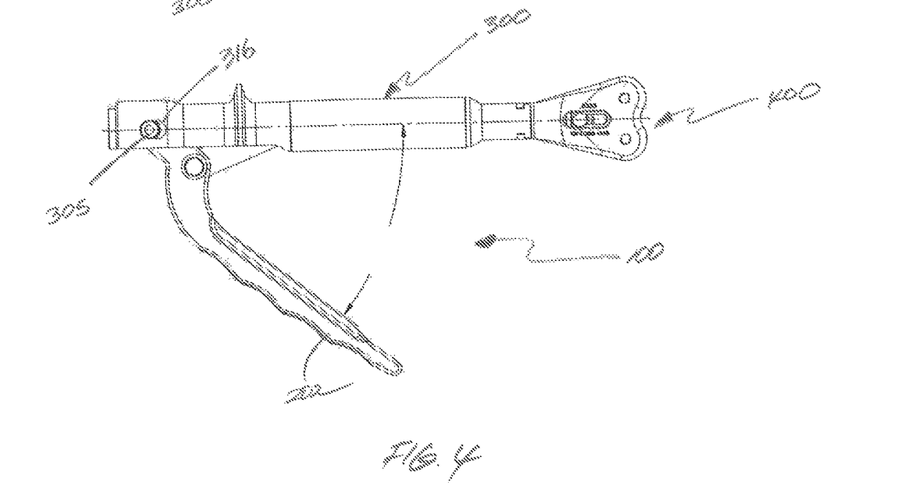
FIG. 4 is a rear view of the spinal plate bender of FIG. 1.
Figure 5:
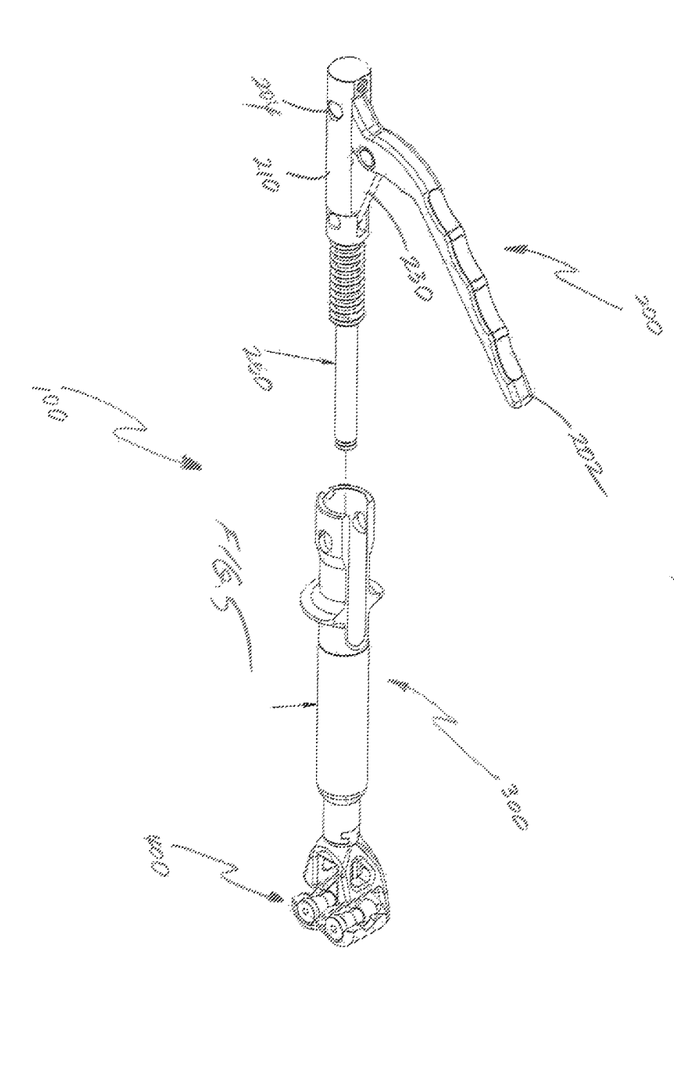
FIG. 5 is a perspective view of the spinal plate bender of FIG. 1, illustrating an actuation assembly and a collet with a head portion separated from each other.
Figure 6:
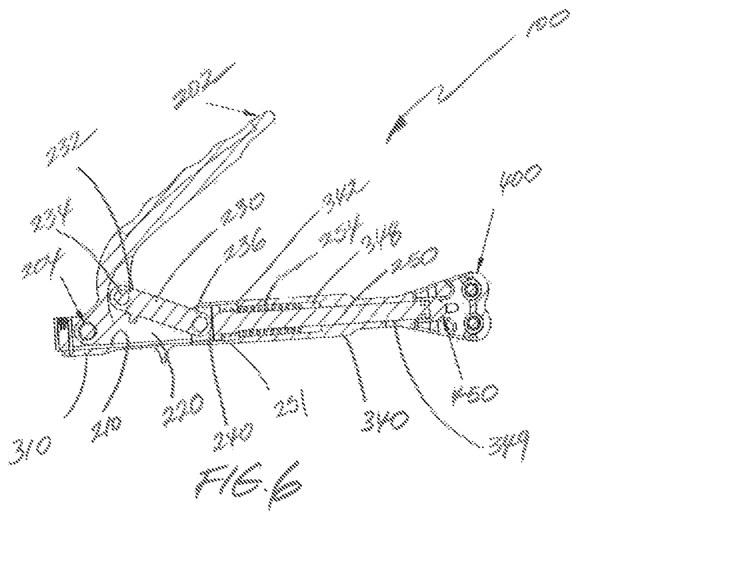
FIG. 6 is a cross-sectional view of the spinal plate bender of FIG. 1.
Figure 7:
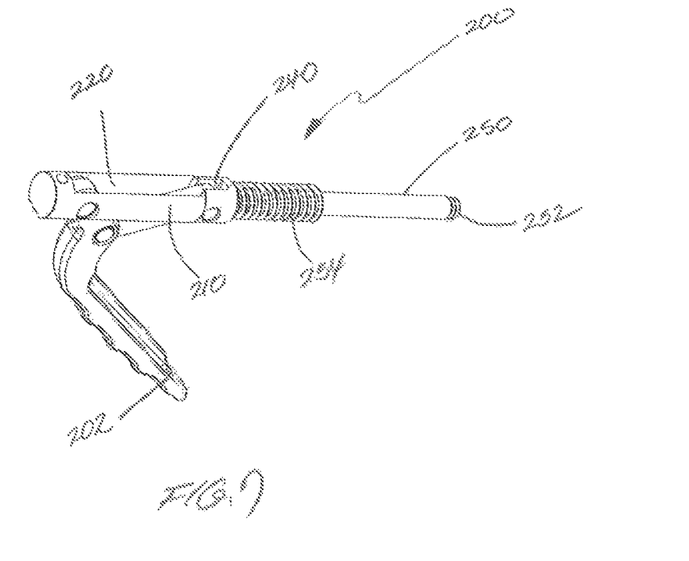
FIG. 7 is a perspective view of the actuation assembly of FIG. 5.

With reference now to FIGS. 5-7, the actuation assembly 200 includes a housing 210 including a chamber 220 configured to receive a portion of a lever 202 and a linkage 230 therein. The lever 202 is pivotably coupled to the housing 210 about a pivot 204 such that the lever 202 is movable between a neutral position (FIG. 9) in which the lever 202 is disposed laterally offset from a longitudinal axis "X-X" (FIG. 9) defined by the collet 300 and defining a maximum angle of, e.g., about 37 degrees, and an actuated position (FIG. 2) in which the lever 202 is substantially parallel to the longitudinal axis "X-X" of the collet 300. The linkage 230 includes first and second ends 232, 236. The first end 232 is pivotably coupled to the lever 202 about a pivot 234, and the second end 236 is pivotably coupled to an actuation shaft 250 configured for axial displacement within the collet 300. Under such a configuration, when the lever 202 is transitioned from the neutral position to the actuated position, the linkage 230 advances the actuation shaft 250 axially within the collet 300.

With continued reference to FIGS. 5-7, the actuation shaft 250 includes a proximal end portion 240 pivotably coupled to the second end 236 of the linkage 230. The actuation shaft 250 extends distally into the head portion 400. In particular, the actuation shaft 250 includes a distal end portion 252 configured to releasably support an anvil portion 450 (FIG. 10) thereto. Under such a configuration, axial displacement of the actuation shaft 250 causes the anvil portion 450 to be axially displaced. The actuation shaft 250 further includes a biasing member 254 such as, e.g., a compression spring, that is supported about the actuation shaft 250. When the lever 202 is in the actuated position, i.e., the actuation shaft 250 is advanced, the biasing member 254 is compressed and will urge the actuation shaft 250 to retract towards a proximal position as the lever 202 is pivoted towards the neutral position, i.e., urging the anvil portion 450 away from a distal position, as will be described. It is contemplated that the length of the actuation shaft 250 may be adjustable in order to change the amount of displacement. Alternatively, the length of linkage 230 may also be adjustable. The adjustable length feature may be achieved through the use of, e.g., a turnbuckle.

Figure 8:
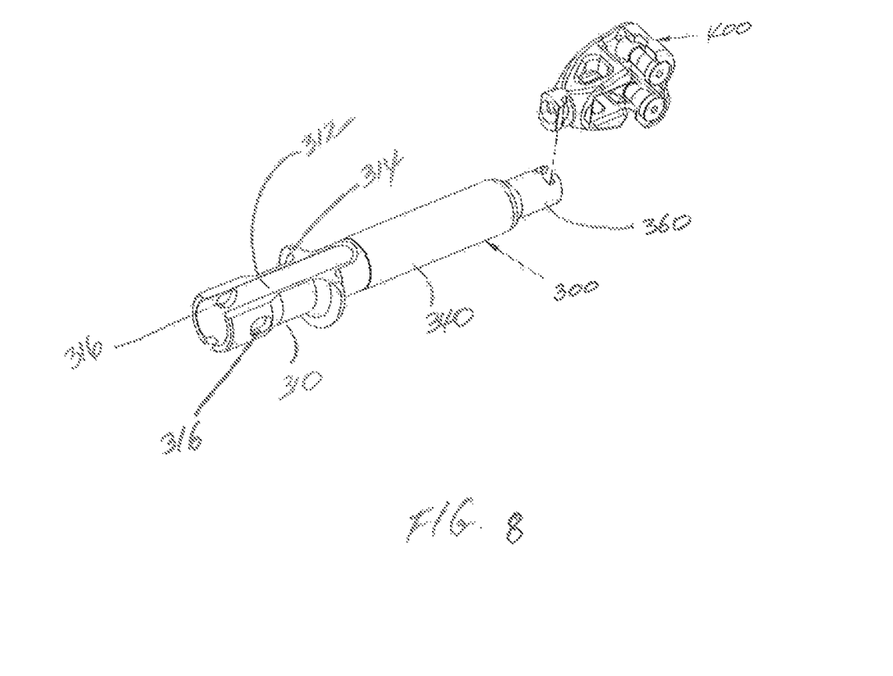
FIG. 8 is a perspective view of the collet and the head portion of FIG. 5, illustrating the head portion detached from the collet.
Figure 9:
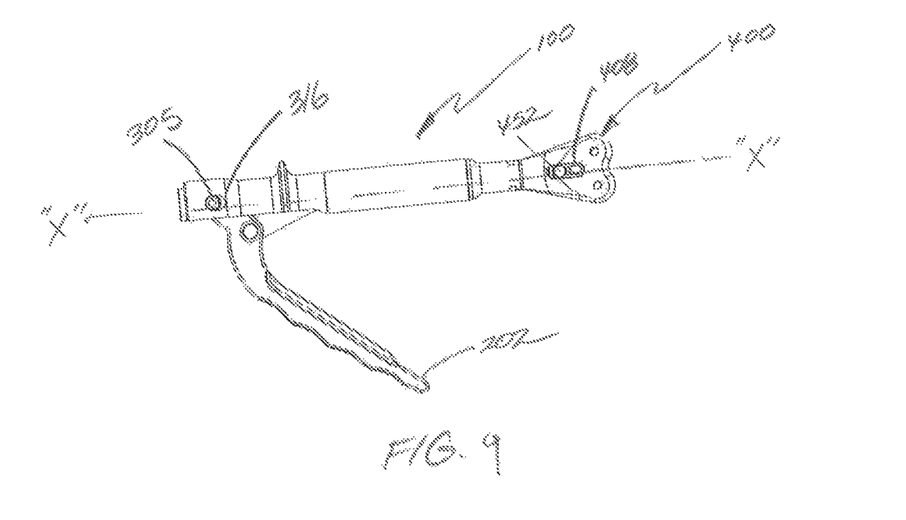
FIG. 9 is a rear view of the spinal plate bender of FIG. 1.

With reference now to FIGS. 8 and 9, the collet 300 includes a proximal section 310, a sleeve section 340 extending distally from the proximal section 310, and a coupling section 360 extending distally from the sleeve section 340. The proximal section 310 is dimensioned to receive the housing 210 (FIG. 7) of the actuation assembly 200. In particular, the proximal section 310 defines a cutout 312 dimensioned to receive the lever 202 and the linkage 230 extending out of the housing 210 during transition between the neutral and actuated positions. The proximal section 310 further includes a flange 314 extending radially outward to facilitate gripping of the collet 300 by the clinician. The proximal section 310 further defines opposing lateral slots 316 dimensioned to receive a pin 305 disposed about the pivot 204 (FIG. 5). The pin 305 is configured to pivotably couple the lever 202 of the actuation assembly 200 to the lateral slots 316 of the proximal section 310 of the collet 300. In particular, each lateral slot 316 has an elongated shape configured to facilitate disassembly of the lever 202 from the collet 300. It is contemplated that a single pin may be used to pivotably couple the lever 202 to the housing 210 of the actuation assembly 200 and the proximal section 310 of the collet 300.

With brief reference back to FIG. 6, the sleeve section 340 of the collet 300 defines a first lumen 342 having a first diameter, a second lumen 348 having a second diameter smaller than the first diameter, and a third lumen 349 having a third diameter smaller than the second diameter. The first diameter is dimensioned to receive the shoulder 251 of the actuation shaft 250. The second diameter of the second lumen 348 is dimensioned to receive a portion of the actuation shaft 250 distal of the shoulder 251 and the biasing member 254 disposed about the portion of the actuation shaft 250. The shoulder 251 at the proximal end portion 240 of the actuation shaft 250 is configured to engage the biasing member 254. The second lumen 348 allows compression of the biasing member 254. During movement of the lever 202 from the neutral position to the actuated position, the distal end of the biasing member 254 contracts the distal end of the second lumen 348 which inhibits further distal movement of the biasing member 254 such that continued axial movement of the actuation shaft 250 compresses the biasing member 254. The third diameter of the third lumen 349 is dimensioned to be substantially equal to the dimensions of the portion of the actuation shaft 250 distal of the shoulder 251 in order to provide stability during axial advancement of the actuation shaft 250.

With reference back to FIG. 8, the head portion 400 is coupled to the coupling section 360 of the collet 300. For example, the head portion 400 may be releasably coupled to the coupling section 360 in order to improve manufacturability and maintenance thereof. In particular, the head portion 400 and coupling section 360 may have a dovetail configuration such that the head portion 400 is coupled to the coupling section 360 at a pre-determined orientation. However, other coupling configurations such as, e.g., bayonet connection, are contemplated. It is contemplated that the head portion 400 may be a user changeable item where a user may select a particular head from a kit. This allows the clinician to select a head that is best suited to the plate to be bent and the procedure at hand. In this manner, for example, the plate bender 100 may be configured for right or left handed use.

Figure 10:
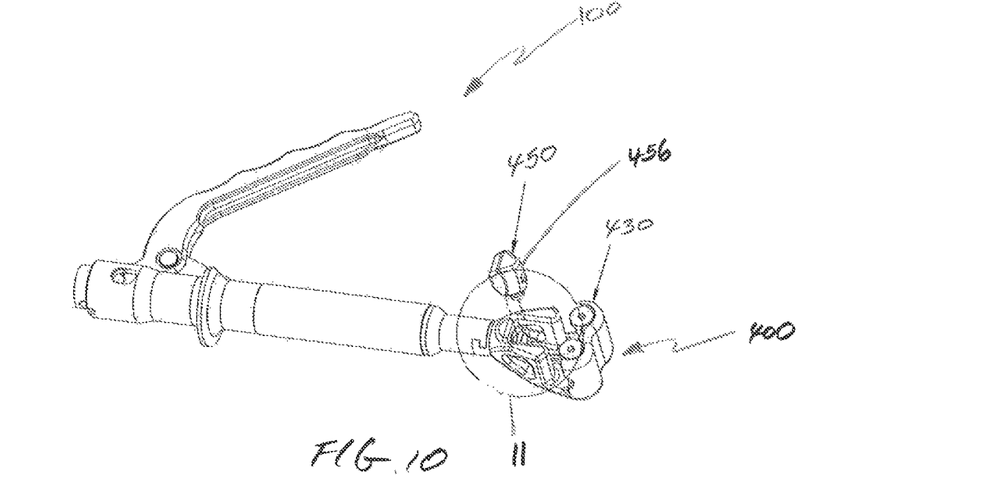
FIG. 10 is a perspective view of the plate ender of FIG. 1, illustrating an anvil portion detached from the head portion.
Figure 11:
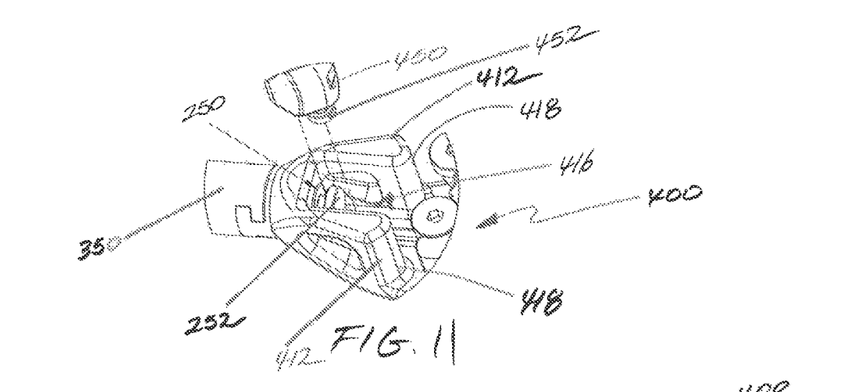
FIG. 11 is an enlarged view of the indicated area of detail of FIG. 10.

With reference now to FIGS. 9-11, the anvil portion 450 is removably coupled to the distal end portion 252 of the actuation shaft 250. The anvil portion 450 may be axially tapered and include a blunt end 456 to facilitate bending of a spinal plate (not shown). The anvil portion 450 includes a pin 452 slidably received in a slot 408 defined axially along a longitudinal axis "X-X" in order to stabilize axial displacement of the anvil portion 450 during bending of the spinal plate to deform the spinal plate in a predetermined manner.

Figures 12, 13:
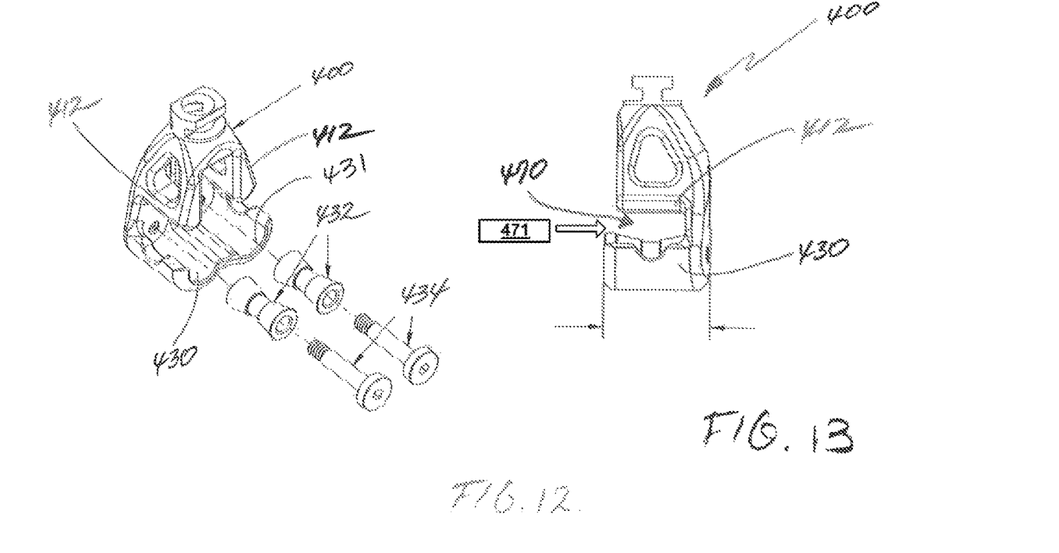
FIG. 12 is an exploded perspective view of the head portion of FIG. 10 with parts separated.
FIG. 13 is a side view of the head portion of FIG. 12.

With reference to FIGS. 11-13, the head portion 400 includes opposing lateral walls 412 defining a gap 416 therebetween. The gap 416 is dimensioned to receive the anvil portion 450 therein. Each lateral wall 412 includes a supporting surface 418 having an arcuate contour configured to support and facilitate bending of the spinal plate thereon. The head portion 400 further includes a roller mount 430 defining arcuate groove 431 configured to rotatably support respective rollers 432 thereon. The rollers 432 may be rotatably secured to the roller mount 430 by respective bolts 434. With particular reference to FIG. 13, the roller mount 430 including the rollers 432, and the lateral walls 412 define a slot 470 dimensioned to receive a spinal plate 471 therein. Under such a configuration, the anvil portion 450 (FIG. 10) travels along the longitudinal axis "X-X" (FIG. 9) extending between the rollers 432 and into the slot 470. Each roller 432 may include an hourglass shape to facilitate bending of the spinal plate when pressed by the anvil portion 450.

In use, the lever 202 (FIG. 9) of the actuation assembly 200 is placed in the neutral position such that the anvil portion 450 (FIG. 11) is in a proximal-most position. At this time, a portion of a spinal plate 471 is inserted into the slot 470 (FIG. 13) defined between the roller mount 430 and lateral walls 412. The clinician transitions the lever 202 to the actuated position (FIG. 2), which causes the actuation shaft 250 to advance such that the anvil portion 450 is pressed against a portion of the spinal plate disposed in the slot 470 and between the rollers 432. The amount of axial displacement of the anvil portion 450 may be determined by the clinician based on the amount of desired curvature of the spinal plate. The clinician may repeat the process as needed to obtain the desired curvature of the spinal plate. Once the desired curvature of the spinal plate is obtained, the clinician may affix the spinal plate to an anatomical structure of the patient by using, e.g., bone screws, hooks, tethers, or spinal rods. The clinician may only partially actuate the plate bender 100 where the lever 202 is only rotated partially between the neutral and actuated positions. It is also contemplated that the clinician may either fully or partially actuate the plate bender 100, but may reposition the plate in the head 400 to create a desired plate configuration.

While several embodiments of the disclosure have been shown in the drawings, it is not intended that the disclosure be limited thereto, as it is intended that the disclosure be as broad in scope as the art will allow and that the specification be read likewise. For example, the plate bender 100 may be used to deform other surgical implants such as, e.g., spinal rods, spinal rod connectors, or rails. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed is:

1. A spinal plate bender comprising:
   an actuation assembly including a housing, a lever pivotably coupled to the housing, a linkage pivotably coupled to the lever, and an actuation shaft operatively coupled with the linkage, the lever transitionable between a neutral position and an actuated position, which, imparts axial displacement to the actuation shaft;
   a collet including a proximal section, a sleeve section extending distally from the proximal section, and a coupling section extending distally from the sleeve section, wherein the collet defines a lumen having a first portion having a first diameter dimensioned to receive a shoulder of the actuation shaft, and a second portion distal of the first portion and having a second diameter smaller than the first diameter; and
   a head portion configured to support a spinal plate, the head portion detachably coupled to the coupling section of the collet, the head portion including lateral walls defining a gap therebetween, an anvil portion coupled to a distal end portion of the actuation shaft configured to advance within the gap defined between the lateral walls to engage the spinal plate to cause bending of the spinal plate supported in the head portion.

2. The spinal plate bender according to claim 1, wherein the head portion defines a slot and the anvil portion includes a pin configured to be slidably received in the slot.

3. The spinal plate bender according to claim 2, wherein the slot extends along a longitudinal axis defined by the collet.

4. The spinal plate bender according to claim 1, wherein the head portion includes a roller mount and rollers rotatably mounted in the roller mount.

5. The spinal plate bender according to claim 4, wherein the rollers and the lateral walls define a slot dimensioned to support a spinal plate therein.

6. The spinal plate bender according to claim 4, wherein each roller has an hourglass shape.

7. The spinal plate bender according to claim 4, wherein the anvil portion of the head portion defines an axis extending between the rollers.

8. The spinal plate bender according to claim 1, wherein the blunt end portion of the anvil portion is tapered.

9. The spinal plate bender according to claim 1, wherein the actuation shaft includes a biasing member disposed about a portion of the actuation shaft distal of the shoulder, the second diameter dimensioned to receive the portion of the actuation shaft and the biasing member.

10. The spinal plate bender according to claim 9, wherein the lumen of the collet further includes a third portion dimensioned to slidably receive the portion of the actuation shaft distal of the shoulder.

11. The spinal plate bender according to claim 1, wherein the collet includes a cutout configured to receive the lever and the linkage extending laterally outward during the transition between the neutral position and the actuated position.

12. The spinal plate bender according to claim 1, wherein the anvil portion has a blunt end portion.

13. A method of bending a spinal plate comprising:
    placing at least a portion of a spinal plate in a slot defined in a head portion of a spinal plate bender, the spinal plate bender including an actuation shaft and an anvil portion configured to engage the spinal plate in a proximal position, the head portion being detachably coupled to the spinal plate bender and including opposing lateral walls defining a gap therebetween within which the anvil portion is configured to advance, the slot defined between rollers of a roller mount on a first side of the slot and terminal ends of the lateral walls opposing the rollers on a second side of the slot; and
    advancing the anvil portion into the head portion such that the anvil portion presses against a portion of the spinal plate in the head portion.

14. The method of bending according to claim 13, wherein placing the spinal plate bender in a neutral position includes placing a lever operatively coupled with the actuation shaft via a linkage, at an acute angle with respect to a longitudinal axis defined by the spinal plate bender.

15. The method of bending according to claim 13, wherein advancing the anvil portion includes placing a lever operatively coupled with the actuation shaft via a linkage, in parallel with a longitudinal axis defined by the spinal plate bender.

16. The method of bending according to claim 13, wherein advancing the anvil portion includes slidably advancing a pin of the anvil portion within a pin slot defined in the head portion.

17. The method of bending according to claim 16, wherein advancing the anvil portion includes advancing the anvil portion in a direction orthogonal to the slot of the head portion.

18. A spinal plate bender comprising:
    an actuation assembly including a housing, a lever pivotably coupled to the housing, a linkage pivotably coupled to the lever, and an actuation shaft operatively coupled with the linkage, the lever transitionable between a neutral position and an actuated position, which, imparts axial displacement to the actuation shaft;
    a collet including a proximal section, a sleeve section extending distally from the proximal section, a coupling section extending distally from the sleeve section, and a cutout configured to receive the lever and the linkage extending laterally outward during the transition between the neutral position and the actuated position; and
    a head portion configured to support a spinal plate, the head portion detachably coupled to the coupling section of the collet, the head portion including lateral walls defining a gap therebetween, an anvil portion coupled to a distal end portion of the actuation shaft configured to advance within the gap defined between the lateral walls to engage the spinal plate to cause bending of the spinal plate supported in the head portion.

19. The spinal plate bender according to claim 18, wherein the head portion defines a slot and the anvil portion includes a pin configured to be slidably received in the slot.

20. The spinal plate bender according to claim 18, wherein the head portion includes a roller mount and rollers rotatably mounted in the roller mount.

* * * * *